United States Patent
Muhlhoff

(10) Patent No.: US 7,842,030 B2
(45) Date of Patent: Nov. 30, 2010

(54) DEVICE AND METHOD FOR DETECTION OF EYE MOVEMENTS

(75) Inventor: Dirk Muhlhoff, Kunitz (DE)

(73) Assignee: Carl Zeiss Meditec AG, Jena (DE)

( * ) Notice: Subject to any disclaimer, the term of this patent is extended or adjusted under 35 U.S.C. 154(b) by 1448 days.

(21) Appl. No.: 11/108,171

(22) Filed: Apr. 15, 2005

(65) Prior Publication Data

US 2005/0251114 A1 Nov. 10, 2005

(30) Foreign Application Priority Data

Apr. 16, 2004 (DE) .................. 10 2004 018 628

(51) Int. Cl.
*A61B 18/18* (2006.01)
(52) U.S. Cl. .................. 606/4; 606/5; 606/10; 128/898
(58) Field of Classification Search ................ 606/107, 606/166, 2–19; 128/898
See application file for complete search history.

(56) References Cited

U.S. PATENT DOCUMENTS

| | | | | |
|---|---|---|---|---|
| 3,864,030 A * | 2/1975 | Cornsweet | ................. | 351/210 |
| 4,848,340 A * | 7/1989 | Bille et al. | .................. | 606/4 |
| 4,887,019 A * | 12/1989 | Reis et al. | .................. | 359/202 |
| 5,481,622 A | 1/1996 | Gerhardt et al. | | |
| 5,984,916 A | 11/1999 | Lai | | |
| 6,110,166 A | 8/2000 | Juhasz | | |
| 6,210,401 B1 * | 4/2001 | Lai | ................. | 606/12 |
| 6,280,436 B1 | 8/2001 | Freeman et al. | | |
| 6,283,954 B1 | 9/2001 | Yee | | |
| 6,315,773 B1 | 11/2001 | Frey et al. | | |
| 6,367,931 B2 * | 4/2002 | Lai | ................. | 351/209 |
| 6,530,917 B1 | 3/2003 | Seiler et al. | | |
| 6,579,282 B2 * | 6/2003 | Bille et al. | .................. | 606/5 |
| 6,755,817 B1 | 6/2004 | Donitzky et al. | | |
| 6,786,899 B1 * | 9/2004 | Lai | ................. | 606/4 |
| 2001/0025172 A1 * | 9/2001 | Frey et al. | .................. | 606/4 |
| 2004/0039378 A1 * | 2/2004 | Lin | ................. | 606/6 |
| 2004/0092914 A1 * | 5/2004 | Bille | ................. | 606/5 |

FOREIGN PATENT DOCUMENTS

| | | |
|---|---|---|
| DE | 199 04 753 C1 | 9/2000 |
| DE | 199 26 476 A1 | 12/2000 |
| DE | 199 50 791 A1 | 5/2001 |
| DE | 199 50 790 A1 | 6/2001 |
| DE | 100 14 479 A1 | 10/2001 |
| WO | WO 95/27454 | 10/1995 |
| WO | WO 99/18868 | 4/1999 |
| WO | WO 01 28476 A1 | 4/2001 |

* cited by examiner

*Primary Examiner*—Henry M Johnson, III
*Assistant Examiner*—Aisha Hunte
(74) *Attorney, Agent, or Firm*—Patterson Thuente Christensen Pedersen, P.A.

(57) ABSTRACT

In a device for detecting eye movements, used in an eye-surgical instrument, which deflects a pulsed treatment laser beam over the cornea in order to form cut areas in the cornea of the eye, and thus forms a sequence of optical breakthroughs in or on the cornea, wherein an optical unit is provided for monitoring the cornea, it is provided that the optical unit monitors the position of at least one optical breakthrough generated in the cornea and recognizes an eye movement on the basis of a migration movement of the monitored optical breakthrough.

6 Claims, 5 Drawing Sheets

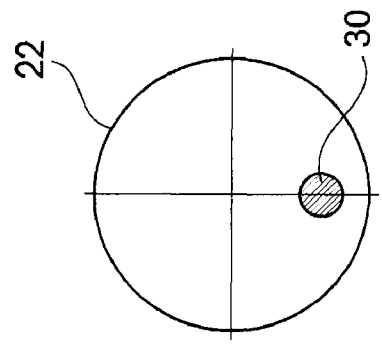
Fig. 3d
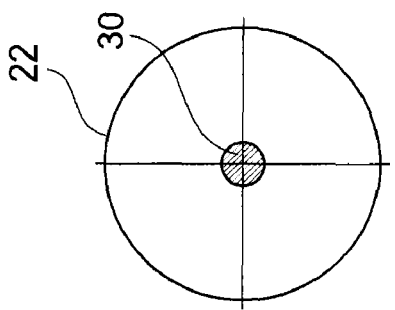
Fig. 3c
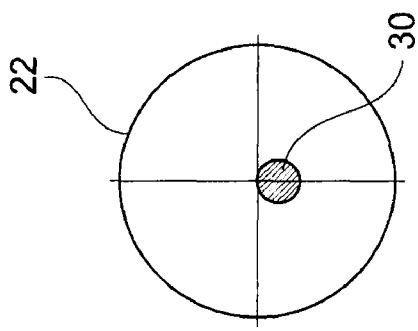
Fig. 3b
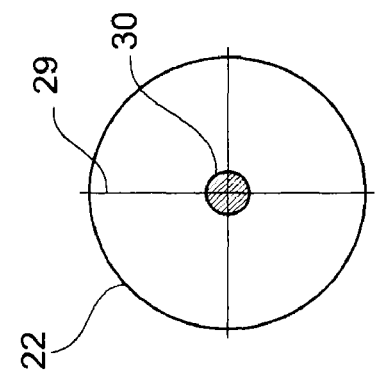
Fig. 3a
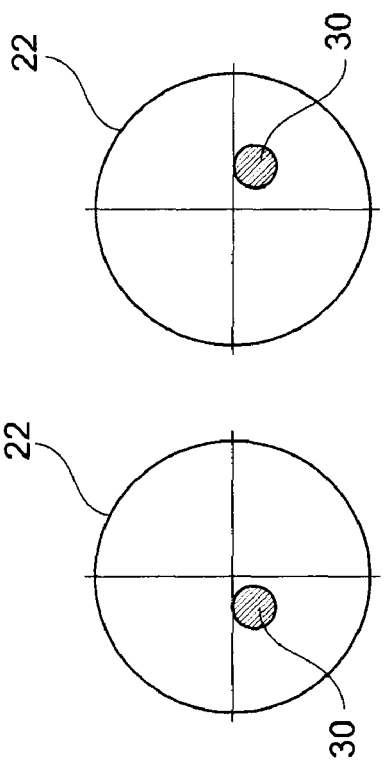
Fig. 3f
Fig. 3e

DEVICE AND METHOD FOR DETECTION OF EYE MOVEMENTS

FIELD OF THE INVENTION

The invention relates to a device for detecting eye movements, used in an eye-surgical instrument which, in order to form cut areas in the cornea of the eye, deflects a pulsed treatment laser beam via the cornea and thereby generates a series of optical breakthroughs in or on the cornea, wherein an optical unit is provided for monitoring the cornea. The invention further relates to a method of detecting eye movements in an eye-surgical method which, in order to form cut areas in the cornea of the eye by advancing a pulsed treatment laser beam, generates a series of individual optical breakthroughs, wherein the cornea is optically sensed.

BACKGROUND OF THE INVENTION

Ophthalmological operations on the cornea of the eye require exact knowledge of the position of the eye. There are principally two approaches for this purpose. First, the cornea of the eye can be spatially fixed by pressing a planar contact element onto it. This approach has the advantage that an exact alignment of the eye to the surgical instrument is possible. Disadvantages are an increase in intraocular pressure and a certain inconvenience for the patient.

Another approach aims to detect and adjust for movements of the eye during an operation. This approach also known as "tracking" has been realized in many ways in the prior art. Thus, for example, U.S. Pat. No. 6,280,436 or U.S. Pat. No. 5,481,622 describe the observation of the eye using a video camera. The position of the pupil is determined on the basis of the video image and an eye movement is derived from shifts in position. A similar approach is taken by WO 95/27454 which discloses a contact element wherein the contact element, provided as a metal ring, replaces the function of the pupil, i.e. a previously known biometry of the contact element is evaluated during video observation for detection of movements. Similar tracking concepts are known from U.S. Pat. Nos. 6,367,291, 6,283,954 and 6,210,401, which either evaluate the transition between the iris and the sclera for detection of movements or which monitor reference marks on a contact glass serving for eye fixation with an independent observation system.

DE 100 14 479 further suggests monitoring the iris of the eye by means of a camera, in order to enable detection of eye movements by an image evaluation method. Another possibility is to measure the distance from the device to several locations on the cornea. For this purpose, U.S. Pat. No. 6,315, 773 uses a laser interferometer.

Tracking methods are in demand, in particular, in laser-surgical instruments, because they advantageously allow working without fixing the eye. In such laser-surgical methods, the treatment laser radiation is focused in or on the tissue so as to cause an optical breakthrough. The treatment laser radiation acts through photodisruption or photoablation.

In the tissue, several processes occur one after the other in time, which are initiated by the treatment laser radiation. If the power density of the radiation exceeds a threshold value, an optical breakthrough occurs, generating a plasma bubble in the tissue. This plasma bubble grows due to expanding gases after the optical breakthrough has formed. If the optical breakthrough is not maintained, the gas generated in the plasma bubble is absorbed by the surrounding tissue and the bubble disappears again. However, this process lasts considerably much longer than the generation of the bubble itself. If a plasma is generated at a tissue interface, which may just as well be located within a tissue structure, tissue is removed from said interface. This is then referred to as photoablation. In the case of a plasma bubble which separates previously connected tissue layers reference is usually made to photodisruption. For the sake of simplicity, all such processes are summarised here by the term optical breakthrough, i.e. this term includes not only the actual optical breakthrough, but also the effects in the tissue resulting therefrom.

It is indispensable for high precision of a laser-surgical method to ensure high localisation of the effect of the treatment laser beams and to avoid, if possible, collateral damage in adjacent tissue. Therefore, it is common in the prior art to apply the treatment laser radiation in a pulsed form, so that the threshold value for the power density of the treatment laser radiation, which is required in order to cause an optical breakthrough, is exceeded only during the individual pulses. High focusing of the laser beam in combination with very short pulses allows the optical breakthrough to be inserted in a tissue in a very punctiform manner.

The use of pulsed treatment laser radiation has become established recently, in particular, for laser-surgical correction of visual deficiencies in ophthalmology. Visual deficiencies of the eye are often due to the fact that the refractive properties of the cornea and of the lense do not cause proper focusing on the retina. In near-sightedness (also referred to as myopia), the focus of the relaxed eye is located in front of the retina, whereas in far-sightedness (also referred to as hyperopia) the focus is located behind the retina.

U.S. Pat. No. 5,984,916 as well as U.S. Pat. No. 6,110,166 describe methods for correction of visual deficiencies by suitably generating optical breakthroughs so as to ultimately influence the refractive properties of the cornea in a selective manner. A multiplicity of optical breakthroughs are placed next to each other such that a lense-shaped partial volume is isolated within the cornea of the eye. The lense-shaped partial volume separated from the remaining corneal tissue is then removed from the cornea by means of a laterally opening cut. The shape of the partial volume is selected such that, after removal, the refractive properties of the cornea are changed so as to cause the desired correction of the visual deficiency.

Of course, in order to isolate the partial volume, it is indispensable to generate the optical breakthroughs at predetermined locations. Uncontrolled eye movements would understandably result in the optical breakthroughs not being generated at the predetermined locations. The aforementioned detection of the eye movement during an operation is thus indispensable for non-contacting laser-surgical methods.

With regard to resolution, the known possibility can be realized in a limited or insufficient or very complex manner only. Moreover only very few approaches allow detection of a rotation of the eye about the optical axis. Therefore, it is an object of the invention to enable improved detection of eye movements with reduced complexity.

SUMMARY OF THE INVENTION

The object is achieved using a device of the above-mentioned type, wherein, in order to detect eye movements, the structure of the cornea is sensed in a measuring spot, which is located within a zone of cut areas, in which the optical breakthroughs are generated, and which measuring spot is smaller than the zone of cut areas. The object is further achieved by a method of the above-mentioned type, wherein, in order to detect eye movements, the structure of the cornea is sensed in a measuring spot, which is located within a zone of cut areas, in which the optical breakthroughs are generated, and which is smaller than the zone of cut areas.

Thus, the method according to the invention is a measuring method which, although being effected during a surgical method, does not have any surgical or therapeutic effect itself.

Thus, according to the invention, the cornea is optically sensed in a small measuring spot and is monitored for an eye movement on the basis of structures in the cornea. This may preferably be effected by the optical unit using a generated optical breakthrough as a structure and monitoring the position of at least one of the optical breakthroughs generated in the cornea and detecting an eye movement on the basis of a migration movement of the monitored optical breakthrough.

Accordingly, the concept of the invention departs from the approach according to the prior art and, for the first time, uses a partial area of the cornea during operation of the surgical instrument for detection of an eye movement. The structure used for detection of eye movements may be artificially generated in the cornea or may also be present naturally. In particular, a generated optical breakthrough may be used directly for detection. In this case, the detection of the eye movement uses the effects of the laser-surgical instrument itself and takes a more direct course than if geometrical dimensions (on the pupil, the iris, distances to the instrument) are referred to.

In doing so, monitoring of the position of the corneal structures, for example of an optical breakthrough, also enables detection of rotations of the eye about the optical axis, which are inherently difficult to recognize, as long as a structure is monitored which is not located exactly on the optical axis. However, this special case practically never applies.

This approach according to the invention is realized, in particular, by monitoring the position of an optical breakthrough. In principle, the migration movement of the monitored structure directly provides a measure for the eye movement. If the measuring spot is not moved relative to the eye, any migration of the position of the monitored structure will be due to an eye movement, i.e. the migration movement is a direct measure for the direction and speed or amount of the eye movement. In observing the position of the structure, e.g. of the optical breakthrough being monitored, it has to be ensured, of course, that there is no confusion with another structure, for example another optical breakthrough. This may be ensured, for example, by pre-forming optical breakthroughs in a certain pattern, for example, in the form of a triangle, a square, a cross, a spiral or line pattern, or the like, guaranteeing unambiguous recognition of the monitored optical breakthrough.

If the measuring spot is passed over the cornea and follows, for example, the generation of the series of optical breakthroughs, a desired migration movement of the corneal structure is to be expected when the eye rests, said movement being caused by the movement of the measuring spot. Any deviation of the detected migration movement from said desired migration movement is then due to an eye movement.

This approach can dispense with arranging the optical breakthrough in a recognizable geometry, if the measuring spot is passed over the cornea synchronously to, at the same speed as and in the same direction as the pulsed laser beam. Due to the known deflection movement, the desired migration movement of optical breakthroughs is then a known value and can easily be taken into consideration. Therefore, a further embodiment includes a deflecting unit that deflects a measuring spot of the optical device via the cornea synchronously to, at the same speed as and in the same direction as the pulsed treatment laser beam, wherein said optical unit detects the position-monitored optical breakthrough in the measuring spot, determines the migration movement of said optical breakthrough and recognizes an eye movement on the basis of a difference between the determined migration movement and a desired migration movement, which is caused by the deflection of the measuring spot.

With reference to the operating method of the device, it is likewise preferred to detect the monitored optical breakthrough in a measuring spot, which is displaced over the cornea synchronously to, at the same speed as and in the same direction as the pulsed treatment laser beam, to determine the migration movement of the detected optical breakthrough and to detect an eye movement on the basis of a difference between the determined migration movement and a desired migration movement, which is caused by advancing the measuring spot.

A particularly simple realization is achieved if the treatment laser beam and the generation of the measuring spot by means of the same deflecting unit are passed over the cornea. The treatment laser beam is then focused within the measuring spot.

The generation of the measuring spot may be achieved in many different ways, for example by imaging a detail of the eye on a suitable detector. In doing so, illumination of the measuring spot may be achieved by means of an additional illumination beam, so that optical breakthroughs are perceivable on the detector with a good signal/noise ratio.

With each pulse of the pulsed treatment laser beam, an optical breakthrough is generated. In order to achieve the desired depth of focus and because the cornea of the eye is material which is transparent to light, a non-linear interaction is usually employed in order to generate the optical breakthrough. This non-linear interaction has the effect that, while an optical breakthrough is being generated, optical detection of optical breakthroughs may be very difficult or even impossible. For reasons of simple realization, it is therefore preferred to monitor the position of the optical breakthroughs generated in the cornea in a clocked manner between pulses of the treatment laser beam. This allows evaluation also of the last-generated and, thus, most recent optical breakthrough. The migration movement then results from a shift in position between two pulses or from a desired position, respectively, which is caused by the further movement of the measuring spot since the last optical breakthrough was generated. Therefore, a further embodiment of the device is preferred, wherein the optical unit detects the optical breakthrough in a clocked manner between pulses of the treatment laser beam and determines the migration movement in the form of a shift in position between two clock pulses, so that the difference is given as a deviation between the actual position and a desired position of the monitored optical breakthrough. With reference to the operating method it is likewise preferred that the detection of the at least one optical breakthrough be effected in a clocked manner between pulses of the treatment laser beam and that the migration movement be determined in the form of a shift in position between two clock pulses, so that the difference is given as a deviation between the actual position and the desired position.

In some applications, it may suffice to detect the fact of an eye movement. An advantageous combination can also be achieved by monitoring a threshold value, i.e. by merely verifying whether the eye movement, i.e. the migration movement or the difference between the actual migration movement and the desired migration movement, exceeds a threshold value. Operation of the device can then be made dependent on the threshold value being kept.

On the other hand, it may be more advantageous for a particularly convenient mode of operation of a surgical instrument, to obtain a signal for the tracking of eye movements by the treatment laser beam. It is therefore preferred that the optical unit detect the amount and the direction of the eye movement. Thus, the device according to the invention measures the amount and the direction of the eye movement. This allows a signal to be obtained which enables automatic tracking of the deflection of the treatment laser beam, so that even in the presence of eye movements, the optical breakthroughs are generated according to a predetermined pattern. Eye movements are then at least partially compensated for.

The beam illuminating the measuring spot may be coupled into a beam path, in which the treatment laser beam is focused in or on the cornea, by means of a beam splitter. Simultaneously, in an advantageous embodiment, the beam splitter may guide radiation, which is scattered back at the optical breakthroughs, to a detector. Depending on its design, said detector does not require a high resolution. In a simple design, a quadrant detector is sufficient, which allows to recognize how a detected optical breakthrough is shifted relative to a desired position (e.g. the center of the quadrant detector).

BRIEF DESCRIPTION OF THE DRAWINGS

The invention will be explained in more detail below, by way of example and with reference to the figures, wherein

FIGS. 3a-3f show exemplary representations of positions of the image of an optical breakthrough during operation of the device according to FIG. 1;

DETAILED DESCRIPTION OF THE INVENTION

Figure 1:
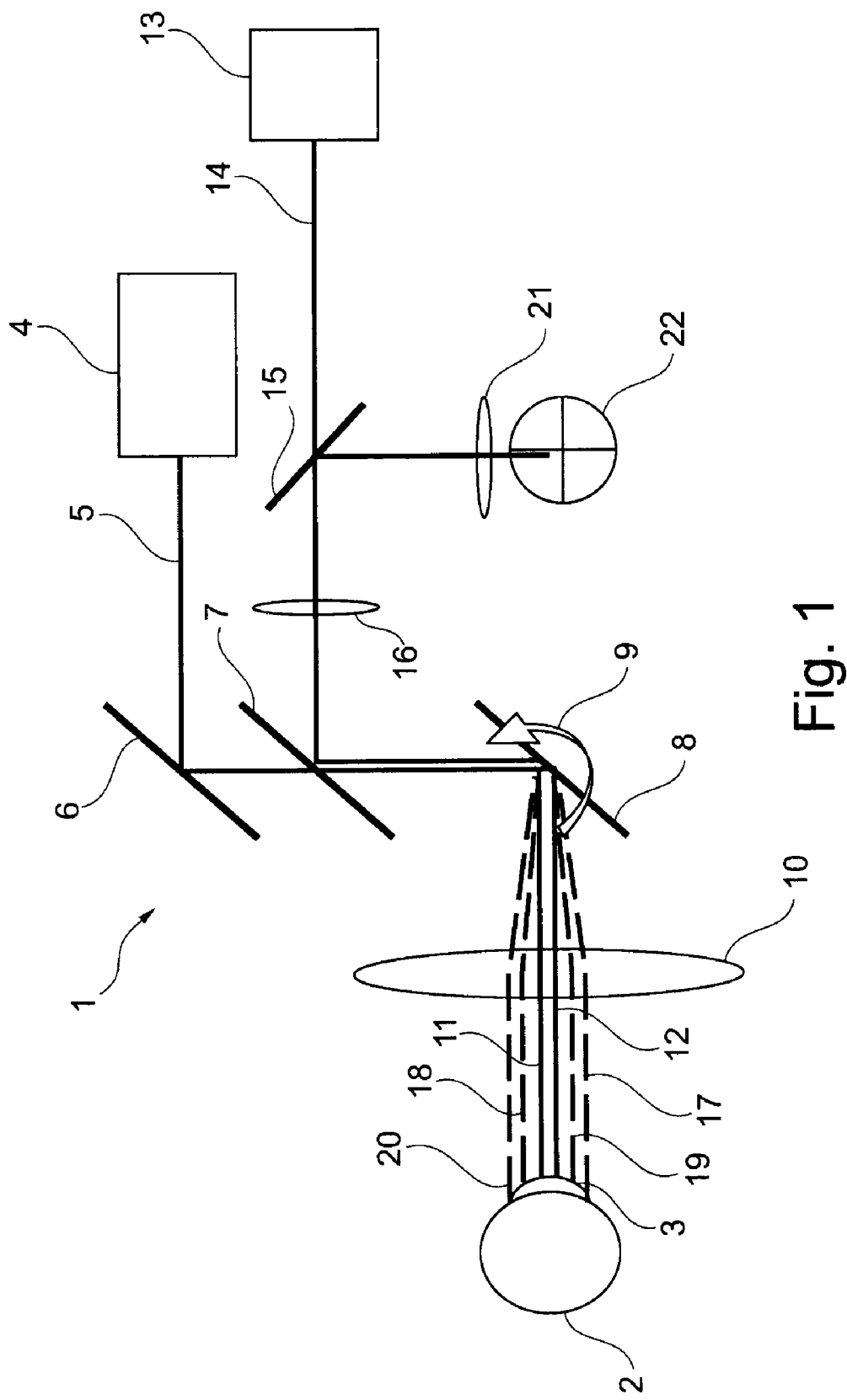
FIG. 1 shows a schematic representation of a surgical instrument comprising a device for detecting eye movements.

FIG. 1 schematically shows a laser-surgical instrument 1, which serves to correct a visual deficiency in the eye 2 of a patient, by removing material from the cornea, such that the refractive characteristic of the cornea changes by a desired amount. The laser-surgical instrument 1 thus works a material which is inherently transparent to laser radiation. Therefore, the pulsed laser radiation is irradiated at a wavelength and focused such that a non-linear absorption is effected and optical breakthroughs are generated. Each individual optical breakthrough initiates a plasma bubble, so that tissue is separated. A partial volume of the stroma of the cornea, namely the material to be removed, is isolated by suitably joining plasma bubbles. The laser-surgical instrument thus functions like a surgical knife, which, without injuring the cornea at the surface, directly cuts material within the transparent cornea of the eye.

For treatment, the laser-surgical instrument 1 directs a treatment beam 5 coming from a treatment laser 4 onto the cornea 3 of the eye 2. The treatment beam 5 is guided, via a deflecting mirror 6 and a splitting mirror 7 (which will be explained later), to a scanner 8 which biaxially deflects the treatment beam 5. An arrow 9 is indicated in FIG. 1 in order to illustrate the deflection process. A scanning objective 10, which is arranged following the scanner 8, focuses the treatment beam 5 into the cornea 3 of the eye 2. During a pulse of the pulsed treatment radiation 5, an optical breakthrough and, thus, a plasma bubble is generated in the focus. The scanning objective 10 is adjustable such that, in combination with the scanner 8, three-dimensional adjustment of the focused treatment beam 5 in the cornea 3 of the eye 2 is achieved. By suitable three-dimensional guiding of the focus many plasma bubbles are joined to each other, in order to form the cut area which isolates the partial volume in the cornea 3.

In order to illustrate the deflection process carried out by the scanner 8, the incident treatment beam 5 is shown in FIG. 1 in an upper position 11 as well as in a lower position 12, which correspond to different angles of deflection of the scanner 8.

In order to also generate optional breakthroughs at predetermined locations in the cornea 3 during eye movements, said eye movements are detected and the scanner 8, including the scanning objective 10, is suitably readjusted. For measurement of the movements of the eye 2, an optical unit is provided which comprises an illumination laser 13 for guiding an illumination beam via a detector beam splitter 15 and imaging optics 16 to the splitting mirror 7, where the illumination beam 14 is coupled into the treatment beam path of the instrument 1. The illumination beam 14 thus also passes via the scanner 8 and the scanning objective 10.

The imaging optics 16 ensure that the illumination beam 14 is incident, expanded in the form of a cone, on the cornea 3. Said cone causes a measuring spot on the cornea 3 which is considerably much larger than the cross-section of the focused treatment beam 5. Because the illumination beam 14 is deflected by the same deflecting means (scanner 8 and scanning objective 10) as the treatment beam 5, the focus of the treatment beam 5 is always at the same location of the measuring spot, which is formed by the expanded illumination beam 14. For example, the focus of the treatment beam 5 may be in the order of magnitude of 3 μm, while the diameter of the measuring spot may be in the order of magnitude of 30 μm. The treatment laser 13 may be, for example, a helium-neon laser or a continuous wave- or pulsed laser diode.

FIG. 1 schematically illustrates the measuring cone in broken lines, wherein the expansions beginning only at the scanner 8 do not correspond to the actual optical conditions, but are only indicated in FIG. 1 for illustration. The measuring cone has an upper limit and a lower limit, which with reference to the representation of FIG. 1, are located above and below the treatment beam 5, respectively. Likewise, FIG. 1 shows a lower measuring cone limit 17 as well as an upper measuring cone limit 18 for the lower position 12 of the treatment beam 5 as well as a lower measuring cone limit 19 and an upper measuring cone limit 20 for the upper position 11 of the treatment beam 5.

The illumination beam 14 directed onto the cornea 3 is scattered more strongly at optical breakthroughs (plasma bubbles) than in the remaining cornea 3. The scattered and back-reflected part of the illumination radiation passes via the scanning objective 10 and the scanner 8 back to the splitting mirror 7, which, due to dichroic properties, couples the back-reflected illumination radiation out via the imaging optics 16 to the detector beam splitter 15, which guides parts of the radiation to detector optics 21, for imaging onto a radiation receiver, which is realized in the embodiment example as a quadrant detector 22. The imaging optics 21 are designed so as to form, on the quadrant detector 22, a sharp image of the plasma bubble/s, which is/are located within the measuring spot 14.

Figure 2:
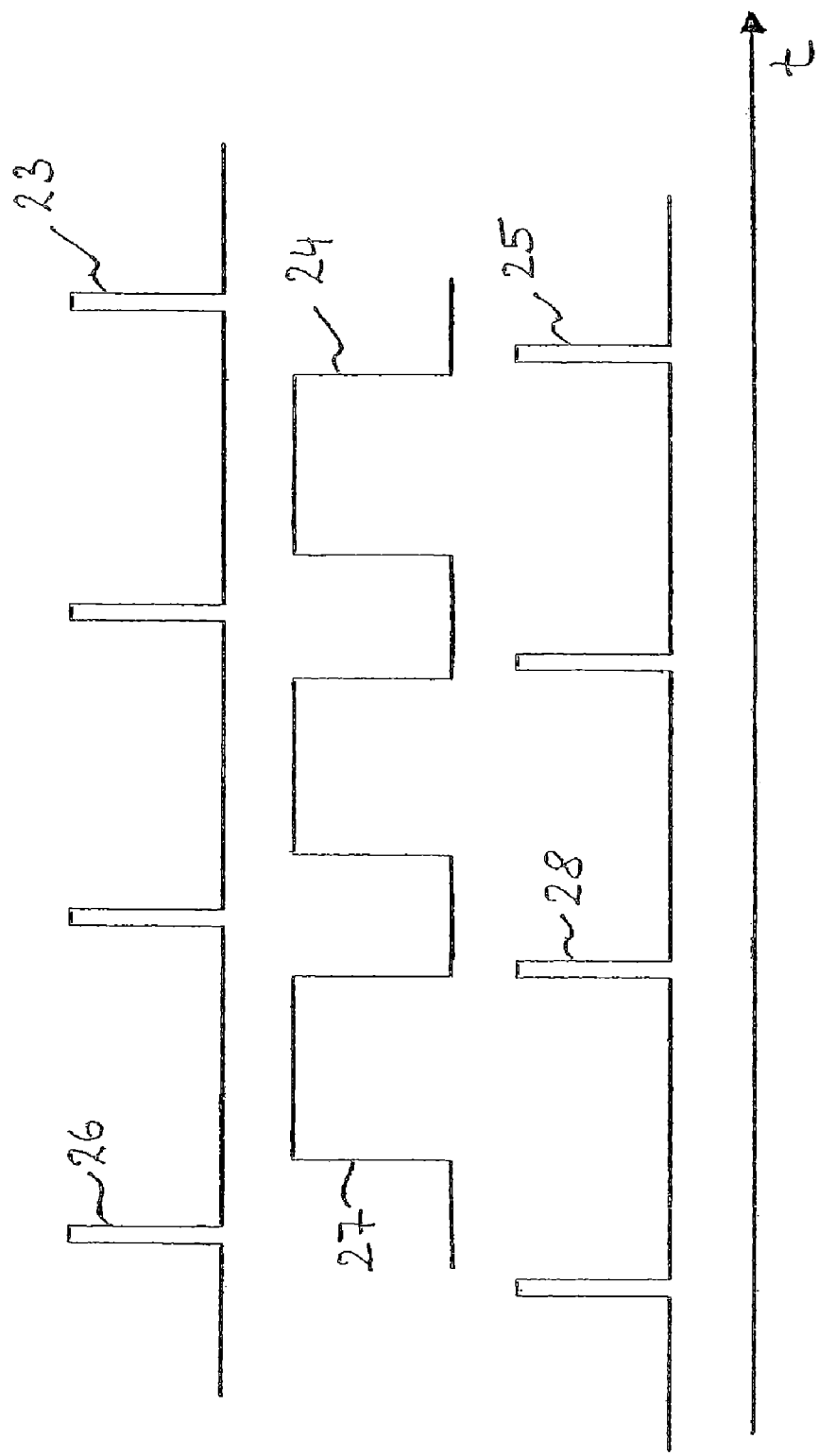
FIG. 2 shows time series which play a role in the operation of the device according to FIG. 1.

The readout of the quadrant detector 22 is effected in a timed manner according to the time series of FIG. 2, namely a treatment pulse sequence 23 of the treatment beam 5, an illumination interval sequence 24 representing the time course of the illumination of the measuring spot by the illumination beam 14, and a trigger sequence 25, by which the readout of the quadrant detector 22 is controlled. If the treatment interval sequence 24 is at a high level, the illumination is switched on.

As is evident from FIG. 2, a treatment pulse 26 which generates an optical breakthrough within the measuring spot is followed by an illumination interval 27, by which the measuring spot is illuminated. During the illumination interval 27, or immediately thereafter (the representation of FIG. 2 is strongly simplified in this respect), a trigger pulse 28 causes a readout of the quadrant detector 22.

The delay between the treatment pulse 26 and the trigger pulse 28 produces two effects: On the one hand, possibly interfering optical effects have been sufficiently reduced by the treatment pulse 26, for example no interfering radiation can deteriorate the result of measurement by non-linear interactions caused by the treatment pulse 26. On the other hand, the scanner 8 has moved slightly further in the time interval between the treatment pulse 26 and the trigger 28. As a result, the image of the plasma bubble on the quadrant detector 22 has moved slightly. This is schematically represented in FIG. 1 by a back-reflected beam, which does not impinge centrally on the quadrant detector 22. If there is a difference between this expected further movement and the measured movement, there has been an eye movement.

FIGS. 3a-f show this, by way of example, for one single plasma bubble. Each of said FIGS. 3a-f shows a top view of the quadrant detector 22. FIG. 3a relates to the generation of a plasma bubble 30 when the scanner 8 stands still, wherein the point of incidence of the treatment beam 15 is located centrally in the measuring spot of the illumination beam 14 and is centered relative to the optical axis of the imaging onto the centred quadrant detector 22. Consequently, the plasma bubble 30 is located at the center of the cross hairs 29 of the quadrant detector 22. FIG. 3b shows the same conditions during operation of the scanner 8. Due to the time delay between the treatment pulse 26 and the trigger pulse 28, the scanner 8 has moved slightly further during evaluation of the quadrant detector 22, i.e. the image of the plasma bubble 30 appears to have moved down on the quadrant detector 22, for example by 10 μm.

However, if the image of the plasma bubble 30 is located closer to the center of the cross hairs 29 than would be expected, the eye has moved in the direction of the scanning movement.

FIG. 3d shows the detection of an eye movement opposed to the scanning movement, so that the image of the plasma bubble 30 is much further away from the center of the cross hairs 29 of the quadrant detector 22 than it should be when the eye is at rest (FIG. 3b).

FIGS. 3e as well as 3f relate to those cases of lateral eye movements which result in a lateral offset of the image of the plasma bubble 30 relative to the cross hairs 29 of the quadrant detector 22.

Figure 4A:
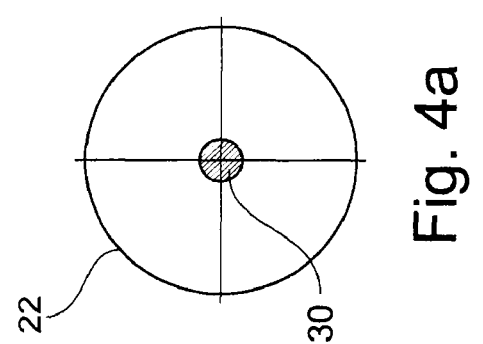
FIGS. 4a-4f show representations similar to FIGS. 3a-f, wherein a series of optical breakthroughs is generated.
Figure 4B:
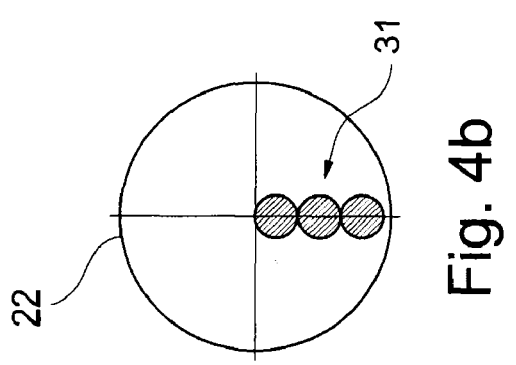
Figure 4C:
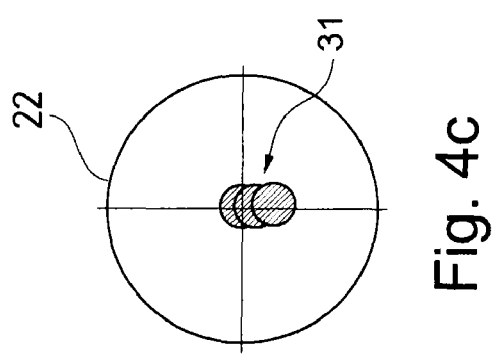
Figure 4D:
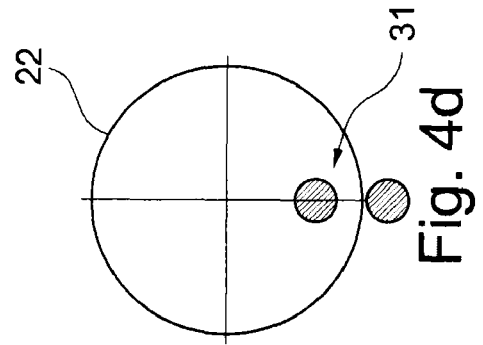
Figure 4E:
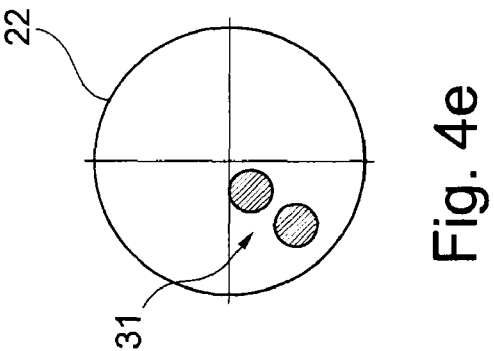
Figure 4F:
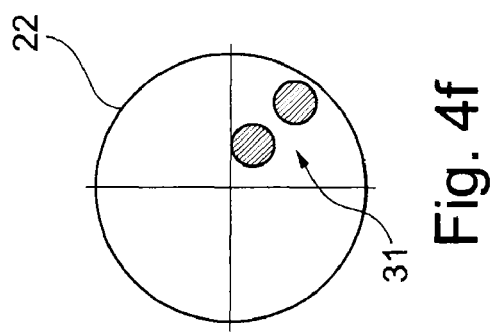

FIGS. 4a-f show the position of the images of several disruption bubbles 30 for a sequence 31 of equidistantly formed disruption bubbles. FIG. 4a corresponds to FIG. 3a, i.e. when the scanner 8 is standing still, the images of the disruption bubbles 30 are located at the center of the quadrant detector 22. FIG. 4b shows the position of the sequence 31 on the quadrant detector 22 during uniform and continuous deflection by the scanner 8 and with the eye resting. In FIG. 4c the images of the plasma bubbles 30 of the sequence 31 are closer to each other than should be the case. The eye moved in the scanning direction while the sequence 31 was being formed. A movement in the opposite direction provides the basis for FIG. 4b, wherein the images of the plasma bubbles 30 are further apart, which has the effect that not all of the images are incident on the quadrant detector 20 anymore. The effects of lateral movements are depicted in FIGS. 4e and 4f.

Figure 5D:
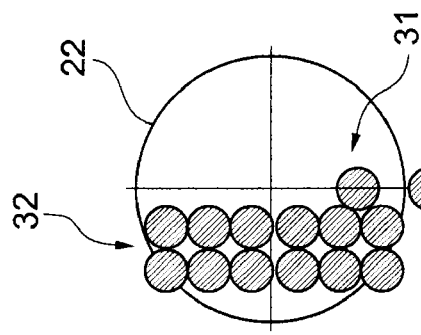
FIGS. 5a-5f show a representation similar to FIGS. 4a-f, wherein a field of optical breakthroughs is generated.
Figure 5C:
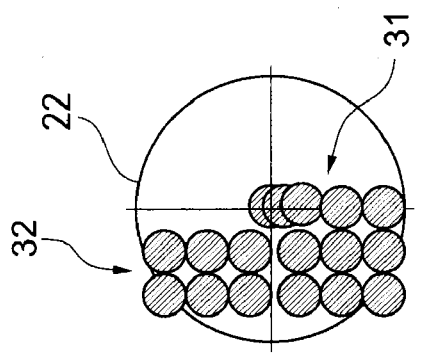
Figure 5B:
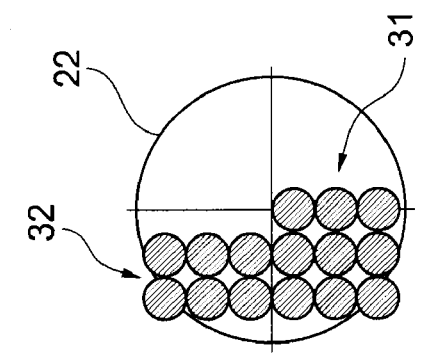
Figure 5F:
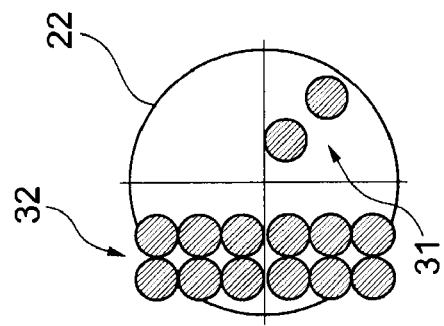
Figure 5A:
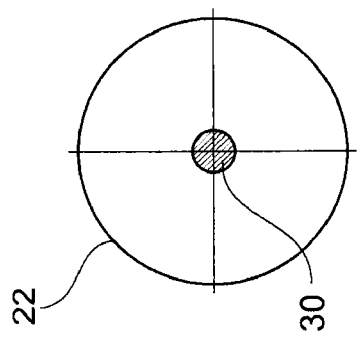
Figure 5E:
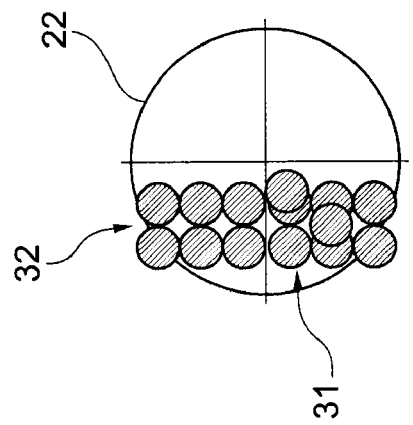

FIGS. 5a-f illustrate analogous conditions during formation of a field 32 of plasma bubbles 30. FIG. 5a again serves to illustrate the conditions for a scanner 8 at rest. FIG. 5b is an image showing continuous and uniform operation of the scanner 8 with the eye at rest. FIGS. 5c-f correspond to FIGS. 4c-f. As regards the last three plasma bubbles 30 (according to the sequence 31), there has been an eye movement in each case, which leads to an undesired lateral displacement of the plasma bubbles 30.

Instead of the horizontal axis of the quadrant detector 22, which is perpendicular to an advancing direction of the scanner 3 in FIGS. 3a-5f, a quadrant detector rotated about 45° may also be used. In some cases, this will facilitate evaluation of the signal of the quadrant detector. Alternatively it is also conceivable to use differently structured detectors or to employ multiple quadrant detectors, whose signals are suitably linked with each other.

The invention claimed is:

1. A method of detecting eye movements
   the method comprising: generating an optical breakthrough in the cornea with a pulsed treatment laser beam in a measuring spot;
   determining a first position of the optical breakthrough within the measuring spot;
   displacing the measuring spot over the cornea substantially synchronously, at
   substantially the same speed and in substantially the same direction as the pulsed treatment laser beam;
   predicting an expected second position of the optical breakthrough in the displaced measuring spot;
   determining a second position of the optical breakthrough within the measuring spot; and
   recognizing an eye movement based on a shift of the second position of the optical breakthrough as compared to the expected second position of optical breakthrough within the measuring spot.

2. The method as claimed in claim 1, further comprising focusing the laser treatment beam within the measuring spot.

3. The method as claimed in claim 1, further comprising
   detecting the at least one optical breakthrough in a timed manner between pulses of the laser treatment beam, and determining the shift based on a difference in position of the at least one optical breakthrough between two clock pulses.

4. The method as claimed in claim 1, further comprising determining the speed and direction of the eye movement.

5. The method as claimed in claim 4, further comprising the steps of at least partially compensating for the eye movement by adjusting an advance of the laser treatment beam.

6. The method as claimed in claim 1, further comprising interrupting or switching off the pulsed laser treatment beam during an eye movement exceeding a threshold value.

* * * * *

UNITED STATES PATENT AND TRADEMARK OFFICE
CERTIFICATE OF CORRECTION

PATENT NO. : 7,842,030 B2
APPLICATION NO. : 11/108171
DATED : November 30, 2010
INVENTOR(S) : Dirk Muhlhoff et al.

Page 1 of 1

It is certified that error appears in the above-identified patent and that said Letters Patent is hereby corrected as shown below:

Col. 8, lines 55-56, claim 5 delete "the steps of".

Signed and Sealed this
Seventeenth Day of May, 2011

David J. Kappos
*Director of the United States Patent and Trademark Office*

UNITED STATES PATENT AND TRADEMARK OFFICE
CERTIFICATE OF CORRECTION

PATENT NO.        : 7,842,030 B2
APPLICATION NO.   : 11/108171
DATED             : November 30, 2010
INVENTOR(S)       : Dirk Mühlhoff et al.

Page 1 of 1

It is certified that error appears in the above-identified patent and that said Letters Patent is hereby corrected as shown below:

Title Page, Item [75] Inventor Name:
Please correct the last name to read "Mühlhoff".

Signed and Sealed this
Twenty-fourth Day of April, 2012

David J. Kappos
*Director of the United States Patent and Trademark Office*